(12) United States Patent
Gawtrey et al.

(10) Patent No.: US 8,574,553 B2
(45) Date of Patent: Nov. 5, 2013

(54) AEROSOL WAX-EFFECT STYLING COMPOSITIONS AND METHODS FOR STYLING AND SHAPING KERATINOUS FIBERS

(75) Inventors: Jonathan Gawtrey, Boulogne (FR); Cécile Bebot, Clichy (FR); Céférino Rodrigues, Montreuil (FR)

(73) Assignee: L'Oreal, Paris (FR)

( * ) Notice: Subject to any disclaimer, the term of this patent is extended or adjusted under 35 U.S.C. 154(b) by 95 days.

(21) Appl. No.: 12/696,477

(22) Filed: Jan. 29, 2010

(65) Prior Publication Data

US 2010/0269844 A1 Oct. 28, 2010

Related U.S. Application Data

(60) Provisional application No. 61/154,855, filed on Feb. 24, 2009.

(30) Foreign Application Priority Data

Jan. 30, 2009 (FR) ...................... 09 50605

(51) Int. Cl.
*A61K 8/00* (2006.01)
*A61K 9/00* (2006.01)
*A61K 8/18* (2006.01)
*A61Q 5/00* (2006.01)
*A61Q 7/00* (2006.01)

(52) U.S. Cl.
USPC .............................................. 424/47; 132/202

(58) Field of Classification Search
USPC ............................................ 424/47; 132/202
See application file for complete search history.

(56) References Cited

U.S. PATENT DOCUMENTS

| | | | |
|---|---|---|---|
| 4,223,009 A | | 9/1980 | Chakrabarti |
| 4,243,657 A | * | 1/1981 | Okumura et al. ............... 424/47 |
| 2004/0141926 A1 | * | 7/2004 | De Carvalho et al. ......... 424/47 |
| 2007/0053847 A1 | | 3/2007 | Braeutigam |

OTHER PUBLICATIONS

French Search Report for FR 0950605, dated Sep. 25, 2009.
English language abstract of JP 2002-370947, Dec. 24, 2002.

* cited by examiner

*Primary Examiner* — Fereydoun G Sajjadi
*Assistant Examiner* — Genevieve S Alley
(74) *Attorney, Agent, or Firm* — O'Brien Jones, PLLC

(57) ABSTRACT

The present disclosure relates to a hair cosmetic composition comprising: at least one anionic fixing polymer, at least one polyol, at least one liquid fatty alcohol, at least one lower $C_1$-$C_4$ monoalcohol, and at least one propellant gas, comprising a water content of less than 10% by weight, with respect to the total weight of the composition, and wherein the hair cosmetic composition is packaged in an aerosol device. Also disclosed herein is a the use of this composition, as well as a method for styling and shaping the hair, such as providing hair with a styling effect.

22 Claims, No Drawings

AEROSOL WAX-EFFECT STYLING COMPOSITIONS AND METHODS FOR STYLING AND SHAPING KERATINOUS FIBERS

This application claims benefit of U.S. Provisional Application No. 61/154,855, filed Feb. 24, 2009. This application also claims benefit of priority under 35 U.S.C. §119 to French Patent Application No. 0950605, filed Jan. 30, 2009.

The present disclosure relates to a hair cosmetic composition, packaged in an aerosol device, comprising at least one anionic fixing polymer, at least one polyol, at least one liquid fatty alcohol, at least one lower $C_1$-$C_4$ monoalcohol, and at least one propellant gas.

The present disclosure also relates to a cosmetic styling method comprising the application of the cosmetic composition to keratinous fibers, for example human keratinous fibers, such as the hair, and to the uses of this composition in styling, for instance for conferring a wax effect on keratinous fibers.

Hair products known for hair shaping and/or form retention in the cosmetics market are spraying compositions, such as lacquers and sprays. They are generally composed of a propellant and of a liquid phase comprising, in a cosmetically acceptable medium, at least one fixing component, the function of which is to form joins between the individual hairs, as a mixture with various cosmetic adjuvants. Generally, the cosmetically acceptable medium may be an alcoholic or aqueous/alcoholic medium and the propellant is a liquefied gas under reduced pressure or dissolved in the liquid phase.

For essentially ecological reasons, a need exists to reduce the content of volatile organic compounds (VOCs), such as ethanol, present in these compositions. However, this reduction in the amount of VOCs should not take place at the expense of the properties of hair shaping and of form retention of the hair.

Wax-effect styling products are, for example, predominantly provided in the general form of viscous pastes which are applied to the hair with the hands. Generally, these products are packaged in tubes or in containers provided with a lid. However, these packaging devices are not always entirely satisfactory, for instance, these devices may not always make it possible to easily deliver the composition in the required amount, and the composition may often be applied in an excessively large amount in comparison with the amount necessary or desired. Furthermore, it may be difficult to obtain a homogenous distribution of the composition over the whole of the area to be treated.

Thus, there is still a need for providing hair cosmetic compositions which can provide keratinous fibers with a wax effect, and avoid at least one of the abovementioned disadvantages.

Wax-effect compositions packaged as aerosols, are for example, disclosed in U.S. Patent Application Publication No. US 2007/0053847 and French Patent Application No. FR 2846880.

The present inventors have therefore discovered that the anhydrous cosmetic composition according to the present disclosure, may make it possible to contribute a wax effect to keratinous fibers, while it may avoid at least one of the disadvantages of the prior art.

Accordingly, the compositions disclosed herein may make it possible to confer, on the hair, a styling effect without rendering it lank. Moreover, the compositions in accordance with the present disclosure, may make it possible to construct and to model the hairstyle while contributing styling, volume, manageability, and sheen.

Therefore, one aspect of the present disclosure is a hair cosmetic composition comprising:
  at least one anionic fixing polymer,
  at least one polyol,
  at least one liquid fatty alcohol,
  at least one lower $C_1$-$C_4$ monoalcohol,
  at least one propellant gas, and
  comprising a water content of less than 10% by weight, with respect to the total weight of the composition, and
  wherein the hair cosmetic composition is packaged in an aerosol device.

Another aspect of the present disclosure relates to a method for styling keratinous fibers, for instance, human keratinous fibers, such as the hair, employing the compositions disclosed herein, packaged in an aerosol device.

Yet another aspect of the present disclosure is the use of the cosmetic compositions disclosed herein for the styling or shaping of keratinous fibers, for example human keratinous fibers, such as the hair, for instance, providing keratinous fibers with a styling effect.

The compositions according to the present disclosure, for instance, are easy to prepare and to apply.

In addition, the compositions according to the present disclosure may make it possible to confer natural and lasting form retention on the hairstyle.

As disclosed herein:

"wax-effect composition" is understood to mean a composition intended to maintain and/or fix keratinous fibers to one another via a certain greasy effect, without the hardening contributed by fixing sprays, while keeping the natural sheen of the keratinous fibers, such as human keratinous fibers, for example the hair; and "hair cosmetic composition" is understood to mean a composition for fixing and/or maintaining keratinous fibers, for instance, human keratinous fibers, such as the hair, compositions for caring for keratinous fibers, compositions for conditioning keratinous fibers, such as compositions intended to contribute softness to keratinous fibers, and compositions for making up keratinous fibers.

The hair compositions according to the present disclosure can be used in a rinse-out or leave-in application. In at least one embodiment, the presently disclosed composition is used in a leave-in application.

The composition according to the present disclosure wherein anionic fixing polymers, polyols and liquid fatty alcohols are combined makes it possible to obtain aerosols with a low content of VOCs, such as with a low content of lower $C_1$-$C_4$ alcohols. Specifically, the VOC content of the composition is, in at least one embodiment, less than or equal to 55% by weight, such as less than or equal to 50% by weight, for example, less than or equal to 45% by weight, with respect to the weight of the composition.

Anionic fixing polymers and their mixtures known in the art can be used in the compositions according to the present disclosure.

As used herein, "fixing polymer" is understood to mean any polymer which makes it possible to confer a shape on the hair or to maintain the hair in a given shape.

The fixing polymers according to the present disclosure can be soluble in the cosmetically acceptable medium or insoluble in the same medium and, in this case, can be used in the form of dispersions of solid or liquid polymer particles (latex or pseudolatex).

The at least one anionic fixing polymer can be chosen from, for example polymers comprising at least one group derived from carboxylic, sulphonic or phosphoric acid and having a number-average molecular weight ranging from 500 to 5,000,000.

The carboxyl groups can be derived from, for instance, unsaturated mono- or dicarboxylic acid monomers, such as those corresponding to the formula:

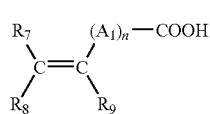

(I)

wherein n is an integer ranging from 0 to 10, $A_1$ is a methylene group, optionally connected to the carbon atom of the unsaturated group or to the neighbouring methylene group when n is greater than 1 via a heteroatom, such as oxygen or sulphur, $R_7$ is chosen from a hydrogen atom, phenyl groups and benzyl groups, $R_8$ is chosen from a hydrogen atom, lower alkyl groups, and carboxyl groups, and $R_9$ is chosen from a hydrogen atom, lower alkyl groups, —$CH_2$—COOH, phenyl groups, and benzyl groups.

In the abovementioned formula, a lower alkyl group is chosen from, for example, groups having 1 to 4 carbon atoms, such as methyl and ethyl groups.

For instance, the at least one anionic fixing polymer comprising carboxyl groups according to the present disclosure, may be chosen from, but are not limited to:

A) The copolymers of acrylic acid and of acrylamide sold in the form of their sodium salts under the names RETEN 421, 423 or 425 by Hercules or the sodium salts of polyhydroxycarboxylic acids.

B) Copolymers of acrylic or methacrylic acid with a monoethylenic monomer, such as ethylene, styrene, vinyl esters or esters of acrylic or methacrylic acid, optionally grafted onto a polyalkylene glycol, such as polyethylene glycol, and optionally crosslinked. Such polymers are described, for example in French Patent No. 1 222 944 and German Patent Application No. 2 330 956, the copolymers of this type comprising, in their chain, an optionally N-alkylated and/or -hydroxyalkylated acrylamide unit, such as described, for instance in Luxembourgian Patent Applications Nos. 75370 and 75371, or provided under the name QUADRAMER by American Cyanamid. Non-limiting mention may also be made of the acrylic acid/ethyl acrylate/N-tert-butylacrylamide terpolymers sold, for example under the name ULTRAHOLD® Strong by BASF. Non-limiting mention may also be made of copolymers of acrylic acid and of $C_1$-$C_4$ alkyl methacrylate and terpolymers of vinylpyrrolidone, of acrylic acid and of $C_1$-$C_{20}$ alkyl methacrylate, for example lauryl methacrylate, such as that sold by ISP under the name ACRYLIDONE® LM, and methacrylic acid/ethyl acrylate/tert-butyl acrylate terpolymers, such as the product sold under the name LUVIMER® 100 P by BASF.

Mention may also be made in a non-limiting manner of the methacrylic acid/acrylic acid/ethyl acrylate/methyl methacrylate copolymers in aqueous dispersion sold under the name AMERHOLD® DR 25 by Amerchol.

C) Copolymers of crotonic acid, such as those comprising, in their chain, vinyl acetate or propionate units and optionally other monomers, such as allyl or methallyl esters, vinyl ether or vinyl ester of a linear or branched saturated carboxylic acid comprising a long hydrocarbon chain, such as those comprising at least 5 carbon atoms, it optionally being possible for these polymers to be grafted or crosslinked, or also another monomer which is a vinyl, allyl or methallyl ester of an α- or β-cyclic carboxylic acid. Such polymers are described, for instance, in French Patents Nos. 1 222 944, 1 580 545, 2 265 782, 2 265 781, 1 564 110 and 2 439 798. Commercial products comprising such copolymers include, but are not limited to the RESINS 28-29-30, 26-13-14 and 28-13-10 sold by National Starch.

D) Copolymers of $C_4$-$C_8$ monounsaturated carboxylic acids or anhydrides chosen from:

copolymers comprising (i) at least one entity chosen from maleic, fumaric and itaconic acids and anhydrides and (ii) at least one monomer chosen from vinyl esters, vinyl ethers, vinyl halides, phenylvinyl derivatives, and acrylic acid and its esters, the anhydride functional groups of these copolymers optionally being monoesterified or monoamidated. Such polymers are described, for instance in U.S. Pat. Nos. 2,047,398, 2,723,248 and 2,102,113, and GB Patent No. 839 805. Commercial products comprising such polymers include, but are not limited to those sold under the names GANTREZ® AN or ES by ISP;

copolymers comprising (i) at least one entity chosen from maleic, citraconic and itaconic anhydride units and (ii) at least one monomer chosen from allyl and methallyl esters, optionally comprising at least one acrylamide, methacrylamide, α-olefin, acrylic or methacrylic ester, acrylic acid, methacrylic acid, and vinylpyrrolidone group in their chain, the anhydride functional groups of these copolymers optionally being monoesterified or monoamidated.

These polymers are, for example, described in French Patents Nos. 2 350 384 and 2 357 241.

E) Polyacrylamides comprising carboxylate groups.

Homopolymers and copolymers comprising sulpho groups, such as polymers comprising vinylsulphonic, styrenesulphonic, naphthalenesulphonic or acrylamidoalkylsulphonic units, other than the branched sulphonic polyesters used according to the present disclosure.

These polymers can be chosen from, for example:

salts of polyvinylsulphonic acid having a molecular weight ranging from 1,000 to 100,000, as well as copolymers with an unsaturated comonomer, such as acrylic or methacrylic acids and their esters, as well as acrylamide or its derivatives, vinyl ethers and vinylpyrrolidone;

salts of polystyrenesulphonic acid, such as the sodium salts sold, for example, under the names FLEXAN® 500 and FLEXAN® 130 by National Starch. These compounds are described, for instance in French Patent No. FR 2 198 719; and salts of polyacrylamidosulphonic acids, such as those mentioned in U.S. Pat. No. 4,128,631 and the polyacrylamidoethylpropanesulphonic acid sold under the name COSMEDIA POLYMER HSP 1180 by Henkel.

Other suitable examples of the at least one anionic fixing polymer that may be mentioned in accordance with the present disclosure, include, but are not limited to the branched block anionic polymer sold under the name FIXATE G-100 by Lubrizol.

The anionic polymers which can be used according to the present disclosure can also be polycondensates comprising at least one polyurethane block and at least one anionic group. These polycondensates may or may not comprise a polysiloxane block. In at least one embodiment, anionic polyurethanes may be used, for instance, those sold by BASF under the name LUVISET PUR or LUVISET Si PUR.

The at least one anionic polymer which can be used according to the present disclosure may also be chosen from polymers comprising a silicone backbone and comprising hydrocarbon grafts and polymers comprising a hydrocarbon backbone and comprising silicone grafts, these polymers comprising, in their structure, at least one anionic group. According to at least one embodiment, the grafts are attached to the backbone via a macromonomer such as the VS 30 polymer from 3M.

The at least one anionic fixing polymer according to the present disclosure may be chosen from, for example copolymers of acrylic or methacrylic acid or their salts, copolymers of crotonic acid, copolymers of $C_4$-$C_8$ monounsaturated carboxylic acids or anhydrides, polyacrylamides comprising carboxylate groups, homopolymers or copolymers comprising sulpho groups, anionic polyurethanes and anionic grafted silicone polymers.

According to at least one embodiment, the at least one anionic fixing polymer is chosen from copolymers of acrylic acid with acrylic esters, such as the acrylic acid/ethyl acrylate/N-tert-butylacrylamide terpolymers sold for example under the name ULTRAHOLD® Strong by BASF, copolymers derived from crotonic acid, such as the vinyl acetate/vinyl tert-butylbenzoate/crotonic acid terpolymers and the crotonic acid/vinyl acetate/vinyl neododecanoate terpolymers sold for example under the name RESIN 28-29-30 by National Starch, polymers derived from maleic, fumaric or itaconic acids or anhydrides with vinyl esters, vinyl ethers, vinyl halides, phenylvinyl derivatives, or acrylic acid and its esters, such as the methyl vinyl ether/monoesterified maleic anhydride copolymers sold, for example, under the name GANTREZ® by ISP, the copolymers of methacrylic acid and of methyl methacrylate sold under the name EUDRAGIT® L by Rohm Pharma, the copolymers of methacrylic acid and of ethyl acrylate sold under the name LUVIMER® MAEX or MAE by BASF, the vinyl acetate/crotonic acid copolymers sold under the name LUVISET CA 66 by BASF and the vinyl acetate/crotonic acid copolymers grafted by polyethylene glycol sold under the name ARISTOFLEX® A by BASF, and the polymer sold under the name FIXATE G-100 by Lubrizol.

According to the present disclosure, the at least one anionic fixing polymer is present in a total amount ranging from 0.01 to 7% by weight, for example ranging from 0.1 to 6% by weight, such as ranging from 0.5 to 3% by weight, with respect to the weight of the composition.

The at least one polyol according to the present disclosure is, for example a molecule comprising a $C_3$ to $C_{30}$ hydrocarbon chain optionally interrupted by at least one heteroatom and is substituted by at least two hydroxyl groups.

In at least one embodiment, the hydrocarbon chain of the at least one polyol is not interrupted by a heteroatom; for example, the number of carbon atoms on the hydrocarbon chain is less than 10, such as less than 8.

In another embodiment, the at least one polyol is a glycol, comprising at least two adjacent carbon atoms, each carrying at least one hydroxyl group.

Non-limiting mention may be made, of suitable polyols according to the present disclosure, of propylene glycol, glycerol (glycerine), isoprene glycol, neopentyl glycol, hexylene glycol, polyethylene glycols and their mixtures.

In at least one embodiment, the at least one polyol is chosen from propylene glycol and glycerol.

The composition according to the present disclosure comprises the at least one polyol in a total amount ranging from 10 to 55% by weight, for instance ranging from 15 to 40% by weight, such as ranging from 15 to 35% by weight, with respect to the total weight of the composition.

As used herein, fatty alcohol is understood to mean a hydrocarbon comprising at least 8 carbon atoms and comprising, as a substituent, only a hydroxyl group. For instance, these fatty alcohols do not comprise oxyalkylene groups, such as oxyethylene or oxypropylene groups, or glycerol groups.

The at least one fatty alcohol, according to the present disclosure, which is liquid at a temperature of less than 30° C., is chosen, for example from saturated and unsaturated, linear and branched, liquid $C_{10}$-$C_{30}$ fatty alcohols. In at least one embodiment, the at least one liquid fatty alcohol is branched and/or unsaturated. As used herein, unsaturated is understood to mean comprising at least one unsaturation, such as an ethylenic unsaturation. In another embodiment, the at least one liquid fatty alcohol is chosen from, for instance caprylic alcohol, n-decyl alcohol, isostearyl alcohol, isocetyl alcohol, isoarachidyl alcohol, 2-octyldodecanol, 2-butyloctanol, oleyl alcohol, linoleyl alcohol, linolenyl alcohol and their mixtures.

According to at least one embodiment of the present disclosure, the at least one fatty alcohol is chosen from isostearyl alcohol, isocetyl alcohol and 2-octyldodecanol.

The at least one liquid fatty alcohol according to the present disclosure is present in a total amount ranging from 0.01 to 10% by weight, for example ranging from 0.1 to 10% by weight, such as ranging from 1 to 5% by weight, with respect to the total weight of the composition.

In at least one embodiment, the polyol/fatty alcohol ratio by weight, is greater than 1, for example ranging from 1.5 to 10.

The composition according to the present disclosure is a composition comprising water content in an amount ranging from 0 to 10% by weight, for example ranging from 0 to 5% by weight, such as ranging from 0 to 3% by weight with respect to the total weight of the composition. In at least one embodiment, the composition does not comprise water added deliberately and is anhydrous. The water that may be present in the composition originates from the bound water contributed by the hygroscopic starting materials or by the hydrated molecules introduced into the composition. For example, this bound water may be present in an amount less than 2% of the total weight of the composition.

The composition according to the present disclosure comprises at least one lower $C_1$-$C_4$ monoalcohol in a total amount less than or equal to 55% by weight, for example from 0.01 to 50% by weight, such as from 0.1 to 45% by weight, with respect to the total weight of the composition.

According to the present disclosure, the at least one lower $C_1$-$C_4$ monoalcohol is chosen from ethanol, isopropanol and their mixtures, and in at least one embodiment, the at least one lower monoalcohol is ethanol.

The at least one propellant gas used in the composition according to the present disclosure is chosen from gases which are soluble or insoluble in the composition, such as dimethyl ether, fluorinated or nonfluorinated hydrocarbons, standard liquefied gases or their mixtures. In at least one embodiment, the at least one propellant gas is dimethyl ether.

The composition according to the present disclosure comprises at least one propellant gas in a total amount ranging from 10 to 50% by weight, for example, ranging from 15 to 45% by weight, such as ranging from 20 to 40% by weight, with respect to the total weight of the composition.

The composition according to the present disclosure can additionally comprise at least one additive chosen from, for example, silicones or silicone derivatives in soluble, dispersed or microdispersed form; soluble or insoluble conditioning agents, such as, fatty esters or solid fatty alcohols; treating active principles, moisturizing agents other than the at least one polyol used in the compositions according to the present disclosure, UV screening agents, acids, bases, plasticizing agents, solubilizing agents, preservatives, vitamins and provitamins, dyes, pigments, anionic, cationic, nonionic or amphoteric surface-active agents, cationic, nonionic or amphoteric fixing polymers, fragrances, corrosion inhibitors and their mixtures.

A person skilled in the art will take care to choose the optional additives and their amounts so that they do not interfere with the properties of the compositions of the present disclosure.

Another aspect of the present disclosure is a method for shaping the hair, comprising the application of a cosmetic composition disclosed herein, for example a styling method comprising applying a composition according to the present disclosure to the hair, optionally rinsing the hair, then shaping the hair, and optionally drying the hair.

In at least one embodiment, the method for styling or shaping the hair comprises the application of a cosmetic composition according to the present disclosure, without subsequent rinsing, and then the shaping of the hair.

Notwithstanding that the numerical ranges and parameters setting forth the broad scope of the disclosure are approximations, unless otherwise indicated the numerical values set forth in the specific examples are reported as precisely as possible. Any numerical value, however, inherently contains certain errors necessarily resulting from the standard deviation found in their respective testing measurements.

The following examples serve to illustrate embodiments of the present disclosure without, however, exhibiting a limiting nature.

EXAMPLES

The following compositions were prepared and placed in an aerosol device:

The concentrations are expressed as grams of active materials per 100 grams of composition.

1. Aerosol Compositions in Accordance with the Present Disclosure:

| Components | Composition 1 | Composition 2 |
|---|---|---|
| Vinyl acetate/vinyl tert-butylbenzoate/crotonic acid terpolymer ($^1$) | 2 | 2 |
| AMP ($^2$) | 0.2 | 0.2 |
| Propylene glycol | 6 | 6 |
| Glycerol | 10 | 10 |
| Octyldodecanol ($^3$) | 4 | 4 |
| Ethanol | 42.8 | 42.8 |
| Dimethyl ether | 35 | 11 |
| 1,1-Difluoroethane ($^4$) | 0 | 24 |

($^1$): Anionic fixing polymer: MEXOMERE PW (Chimex)
($^2$): 2-Amino-2-methyl-1-propanol
($^3$): Liquid fatty alcohol
($^4$): DYMEL 152A (DuPont)

The compositions in accordance with the present disclosure were applied to the hair without subsequent rinsing. The treated hair exhibited a satisfactory long-lasting wax effect without rendering it lank.

Furthermore, these inventive compositions did not result in a detrimental change in the properties of the hair; for example, the hair was shiny.

2. Aerosol Composition not in Accordance with the Present Disclosure:

| Components | Composition 3 |
|---|---|
| Vinyl acetate/vinyl tert-butylbenzoate/crotonic acid terpolymer ($^1$) | 2 |
| AMP ($^2$) | 0.2 |
| Propylene glycol | 6 |
| Glycerol | 10 |
| Stearyl alcohol ($^5$) | 4 |
| Ethanol | 42.8 |
| Dimethyl ether | 11 |
| 1,1-Difluoroethane ($^4$) | 24 |

($^5$): Solid fatty alcohol

Composition 3 was applied to the hair without subsequent rinsing. The treated hair did not exhibit a suitable wax effect, such as that obtained with the compositions in accordance with the present disclosure.

Composition 3 resulted in a sticky effect on the hands and dried out the hair without providing a wax effect.

What is claimed is:

1. A hair cosmetic composition comprising:
   at least one anionic fixing polymer,
   at least one polyol,
   at least one liquid fatty alcohol,
   at least one lower $C_1$-$C_4$ monoalcohol,
   at least one propellant gas, and
   comprising a water content of less than 10% by weight, with respect to the total weight of the composition, and wherein the hair cosmetic composition is packaged in an aerosol device.

2. The hair cosmetic composition according to claim 1, wherein the at least one anionic fixing polymer is chosen from copolymers of acrylic or methacrylic acid or their salts, copolymers of crotonic acid, copolymers of $C_4$-$C_8$ monounsaturated carboxylic acids or of $C_4$-$C_8$ monounsaturated carboxylic anhydrides, polyacrylamides comprising carboxylate groups, homopolymers or copolymers comprising sulpho groups, anionic polyurethanes and anionic grafted silicone polymers.

3. The hair cosmetic composition according to claim 1, wherein the at least one anionic fixing polymer is present in a total amount ranging from 0.01% to 7% by weight, with respect to the total weight of the composition.

4. The hair cosmetic composition according to claim 1, wherein the at least one polyol is chosen from propylene glycol, glycerol, isoprene glycol, neopentyl glycol, hexylene glycol, and polyethylene glycols.

5. The hair cosmetic composition according to claim 1, wherein the at least one polyol is present in a total amount ranging from 10 to 55% by weight, with respect to the total weight of the composition.

6. The hair cosmetic composition according to claim 1, wherein the at least one liquid fatty alcohol is chosen from caprylic alcohol, n-decyl alcohol, isostearyl alcohol, isocetyl alcohol, isoarachidyl alcohol, 2-octyldodecanol, 2-butyloctanol, oleyl alcohol, linoleyl alcohol, and linolenyl alcohol.

7. The hair cosmetic composition according to claim 1, wherein the at least one liquid fatty alcohol is chosen from isostearyl alcohol, isocetyl alcohol and 2-octyldodecanol.

8. The hair cosmetic composition according to claim 1, wherein the at least one liquid fatty alcohol is present in a total amount ranging from 0.01 to 10% by weight, with respect to the total weight of the composition.

9. The hair cosmetic composition according to claim 1, wherein the at least one lower $C_1$-$C_4$ monoalcohol is chosen from ethanol, and isopropanol.

10. The hair cosmetic composition according to claim 1, wherein the at least one lower $C_1$-$C_4$ monoalcohol is present in a total amount less than or equal to 55% by weight, with respect to the total weight of the composition.

11. The hair cosmetic composition according to claim 10, wherein the at least one lower $C_1$-$C_4$ monoalcohol is present in a total amount ranging from 0.01 to 50% by weight, with respect to the total weight of the composition.

12. The hair cosmetic composition according to claim 1, wherein the at least one propellant gas is chosen from dimethyl ether, fluorinated or nonfluorinated hydrocarbons, and standard liquefied gases.

13. The hair cosmetic composition according to claim 1, wherein the at least one propellant gas is present in a total amount ranging from 10% to 50% by weight, with respect to the total weight of the composition.

14. The hair cosmetic composition according to claim 1, wherein the weight ratio of the at least one polyol to the at least one fatty alcohol has a value greater than 1.

15. The hair cosmetic composition according to claim 1, further comprising at least one additive chosen from silicones and silicone derivatives in soluble, dispersed or microdispersed form; soluble and insoluble conditioning agents; treating active principles, moisturizing agents other than polyols, UV screening agents, acids, bases, plasticizing agents, solubilizing agents, preservatives, vitamins and provitamins, dyes, pigments, anionic, cationic, nonionic and amphoteric surface-active agents, cationic, nonionic and amphoteric fixing polymers, fragrances, and corrosion inhibitors.

16. A method for shaping the hair, comprising:
applying to the hair a cosmetic composition comprising:
at least one anionic fixing polymer,
at least one polyol,
at least one liquid fatty alcohol,
at least one lower $C_1$-$C_4$ monoalcohol,
at least one propellant gas; and
comprising a water content of less than 10% by weight, with respect to the total weight of the composition, and
wherein the hair cosmetic composition is packaged in an aerosol device,
optionally rinsing the hair;
shaping the hair; and
optionally drying the hair.

17. The method according to claim 16, wherein the hair is not rinsed before shaping the hair.

18. The hair cosmetic composition according to claim 5, wherein the at least one polyol is present in a total amount ranging from 15 to 35% by weight, with respect to the total weight of the composition.

19. The hair cosmetic composition according to claim 8, wherein the at least one liquid fatty alcohol is present in a total amount ranging from 1 to 5% by weight, with respect to the total weight of the composition.

20. The hair cosmetic composition according to claim 11, wherein the at least one lower $C_1$-$C_4$ monoalcohol is present in a total amount ranging from 0.1 to 45% by weight, with respect to the total weight of the composition.

21. The hair cosmetic composition according to claim 13, wherein the at least one propellant gas is present in a total amount ranging from 20% to 40% by weight, with respect to the total weight of the composition.

22. The hair cosmetic composition according to claim 14, wherein the weight ratio of the at least one polyol to the at least one fatty alcohol has a value ranging from 1.5 to 10.

* * * * *